(12) United States Patent
Schreiber et al.

(10) Patent No.: US 8,574,845 B2
(45) Date of Patent: Nov. 5, 2013

(54) METHOD FOR IDENTIFYING AN INCREASED SUSCEPTIBILITY TO ULCERATIVE COLITIS

(75) Inventors: Stefan Schreiber, Kiel (DE); Andre Franke, Keil (DE)

(73) Assignee: Christian-Albrechts-Universitat zu Kiel, Kiel (DE)

( * ) Notice: Subject to any disclaimer, the term of this patent is extended or adjusted under 35 U.S.C. 154(b) by 471 days.

(21) Appl. No.: 12/746,419

(22) PCT Filed: Oct. 8, 2008

(86) PCT No.: PCT/EP2008/008491
§ 371 (c)(1),
(2), (4) Date: Jun. 4, 2010

(87) PCT Pub. No.: WO2010/040365
PCT Pub. Date: Apr. 15, 2010

(65) Prior Publication Data
US 2010/0279297 A1 Nov. 4, 2010

(51) Int. Cl.
*C12Q 1/68* (2006.01)
*C12P 19/34* (2006.01)
(52) U.S. Cl.
USPC ........................................ 435/6.12; 435/91.2
(58) Field of Classification Search
None
See application file for complete search history.

(56) References Cited

PUBLICATIONS

Franke et al. Sequence variants in IL 10, ARPC2 and mlutiple other loci contibute to ulcerative colitis susceptibility. Nature Genetics (2008) vol. 40, No. 11, pp. 1319-1323 (also published online on Oct. 5, 2008).*
Franke et al. Sequence variants in IL 10, ARPC2 and mlutiple other loci contibute to ulcerative colitis susceptibility. Nature Genetics (2008) vol. 40, No. 11, Supplementary methods and materials, pp. 1-48 (also published online on Oct. 5, 2008).*
Webb et al., "*Renal Transplantation in Wiskott-Aldrich Syndrome*", Brief Communications, No. 56, pp. 1585, Dec. 1993.
Croucher et al., "*Haplotype Structure and Association to Crohn's Disease of Card15 Mutations in Two Ethnically Divergent Populations*", European Journal of Human Genetics, No. 11, pp. 6-16, 2003.
Weersma, "*Genetic Susceptibility for Inflammatory Bowel Diseses*", American Journal of Gastroenterol, Chapter 6, pp. 85-96, 2008.
Dupont et al., "*PS: Power and Sample Size Calculation*", Controlled Clinical Trials, No. 18, 1997.
Lennard-Jones, "*Classification of Inflammatory Bowel Disease*", Scandinavian Journal of Gastroenterol, No. 24, Suppl. 170, pp. 2-6,1989.
Truelove et al., "*Course and Prognosis of Crohn's Disease*", Gut, No. 17, pp. 192-201, 1976.
Krawczak et al., "*PopGen: Population-Based Recruitment of Patients and Controls for the Analysis of Complex Genotype-Phenotype Relationships*", Community Genetics, No. 9, pp. 55-61, 2006.
Hampe et al., "*A Genoinewide Analysis Provides Evidence for Novel Linkages in Inflammatory Bowel Disease in a Large European Cohort*", American Journal of Human Genetics, No. 64, pp. 808-816, 1999.
Hampe et al., "*A Genome-lfride Association Scan of Nonsynonymous SNPs Identifies a Susceptibility Variant for Crohn Disease in ATGI6L1*", Nature Genetics, vol. 39, No, 2, pp. 207-211, Feb. 2007.
Stoll et al., "*Genetic Variation in DLG5 is Associated with Inflammatory Bowel Disease*", Nature Genetics, vol. 36, No. 5, pp. 476-480, May 2004.
Franke et al., "*Systematic Association Mapping Identifies Nell1 as a Novel IBD Disease Gene*", PloS One Issue 8, e691, pp. 1-13, Aug. 2007.
Moum et al.,"*Incidence of Ulcerative Colitis and Indeterminate Colitis in Four Counties of Southeastern Norway, 1990-93*", Scandinavian Journal of Gastroenterol, No. 31, pp. 362-366, 1996.
Moum et al., "*Incidence of Crohn's Disease in Four Counties in ,Southeastern Norway, 1990-93*", Scandinavian Journal of Gastroenterol, No. 31, pp. 355-361, 1996.
Onnie et al., "*Associations of Allelic Variants of the Multidrug Resistance Gene (ABCB1 or MDR1) and Inflammatory Bowel Disease and Their Effects on Disease Behavior: A Case-Control and Meta-Analysis Study*", Inflammatory Bowel Disease, vol. 12, No. 4, pp. 263-271- Apr. 2006.
WTCCC, "*Genome-Wide Association Study of 14,000 Cases of Seven Common Diseases and 3,000 Shared Controls*", Nature, vol. 447, pp. 661-678, Jun. 2007.
Vermeire et al., "*Association of Organic Cation Transporter Risk Haplotype with Perianal Penetrating Crohn's Disease but Not with Susceptibility to IBD*", Gastroenterology, No. 129, pp. 1845-1853, 2005.
Stokkers et al., "*Analysis of a Positional Candidate Inflammatory Bowel Disease: NRAMP2*", Inflammatory Bowel Diseases, vol. 6, No. 2, pp. 92-98, 2000.
Dideherg et al., "*An Insertion—Deletion Polymorphism in the Interferon Regulatory Factor 5 (IRF5) Gene Confers Risk of Inflammatory Bowel Diseases*", Human Molecular Genetics, vol. 16, No. 24, pp. 3008-3016, 2007.
Gazouli et al., "*Single Nucleotide Polymorphisms of OCTN1, OCTN2, and DLG5 Genes in Greek Patients with Crohn's Disease*", World Journal of Gastroenterol, vol. 11, No. 47, pp. 7525-7530, 2005.
Gazouli et al, "*Association Between Polymorphism in the Toll-Like Receptor 4, CD14, and CARD15/NOD2 and Inflammatory Bowel Disease in the Greek Population*", World Journal of Gastroenterol, vol. 11, No. 5, pp. 681-685, 2005.
Buch et al., "*A Genome-Wide Association Scan Identifies the Hepatic Cholesterol Transporter ABCG8 as a Susceptibility Factor for Human Gallstone Disease*", Nature Genetics, vol. 39, No. 8, pp. 995-999, Aug. 2007.

(Continued)

*Primary Examiner* — Kenneth R. Horlick
*Assistant Examiner* — David Thomas
(74) *Attorney, Agent, or Firm* — Diederiks & Whitelaw, PLC (57) ABSTRACT

A method is provided for detecting an increased susceptibility to ulcerative colitis by determining the presence of a polymorphism at position 256 of the nucleotide sequence of rs3024505 in which C is substituted by T or the presence of a polymorphism at position 501 of the nucleotide sequence of rs12612347 in which G is substituted by A.

4 Claims, 1 Drawing Sheet

(56) References Cited

PUBLICATIONS de Bakker et al., "*Efficiency and Power in Genetic Association Studies*", Nature Genetics, vol. 37, No. 11, pp. 1217-1223, Nov. 2005.

Barrett et al., "*Haploview: Analysis and Visualization of LD and Haplotype Maps*", Bioinformatics, vol. 21, No. 2, pp. 263-265, 2005.

Teuber et al., "*Improving Quality Control and Workflow Management in High-Throughput Single-Nucleotide Polymorphism Genotyping Environments*", Journal of the Association for Laboratory Automation, No. 10, pp. 43-47, Feb. 2005.

Purcell et al., "*PLINK: A Tool Set for Whole-Genome Association and Population-Based Linkage Analysis*", The American Journal of Human Genetics, vol. 81 pp.559-579, Sep. 2007.

Franke et al., "*Genomizer: An Integrated Analysis System for Genonte-Wide Association Data*", Human Mutation, vol. 27, No. 6, pp. 583-588, 2006.

Rockhill et al., "*Use and Misuse of Population Attributable Fractions*", American Journal of Public Health, vol. 88, No. 1, pp, 15-19, 1998.

Weckx et all "*NovoSNP, A Novel Computational Tool or Sequence Variation Discovery*", Genome Research, No. 15, pp. 436-442, 2005.

Loftus, Jr., "*Clinical Epidemiology of Inflammatory Bowel Disease: Incidence, Prevalence, and Environmental leuences*", Gastroenterology, 126, pp. 1504-1517, 2004.

Bounia et al., "*The Immunological and Genetic Basis of Inflammatory Bowel Disease*", Nature Reviews Immunology, vol. 3, pp. 521-533, Jul. 2003.

Mathew, "*New Links to the Pathogenesis of Crohn Disease Provided by Genome-Wide Association Scans*", Nature Reviews Genetics, pp. 1-6, Oct. 2007.

Duerr et al., "*A Genome-Wide Association Study Identes IL23R as an Inflammatory Bowel Disease Gene*", Science Express, pp. 1-6, Oct. 2006.

Franke et al., "*Replication of Signals from Recent Studies of Crohn's Disease Identifies Previously Unknown Disease Loci for Ulcerative Colitis*", Nature Genetics Advance Online Publication, pp. 1-3, Apr. 2008.

Fisher et al., "*Genetic Determinants of Ulcerative Colitis Include the ECM1 Locus and Five Loci Implicated in Crohn's Disease*", Nature Genetics Advance Online Publication, pp. 1-3, Apr. 2008.

Devlin et al., "*Genomic Control.For Association Studies*", Dept. Of Psychiatry, University of Pittsburgh and Department of Statistics, Carnegie Mellon University, pp. 1-18. 1998.

Stokkers et al., "*HLA-DR and—DQ Phenotypes in Inflammatory Bowel Disease: a Meta-Analysis*", Gut, vol. 45, pp. 395-401, 1999.

Marangoni et al., "*WASP Regulates Suppressor Activity of Human and Murine CD4, CD25 FOXP3 Natural Regulatory T Cells*", The Journal of Experimental Medicine, vol. 204, No. 2, pp. 369-380, Feb. 2007.

van Heel et al, "*Inflammatory Bowel Disease Susceptibility Loci Defined by Genome Scan Meta-Analysis of 1952 Affected Relative Pairs*", Human Molecular Genetics, vol. 13, No. 7, pp. 763-770, 2004.

van der Linde et al., "*A functional Interleukin-10 Mutation itm Dutch Patients with Crohn's Disease*", Digestive and Liver Disease, No. 37, pp. 330-335, 2005.

Balding et al., "*Inflammatory Bowel Disease; the Role of Inflammatory Cytokine Gene Polyinmphisin*", Mediators of Inflammation, No. 13(3), pp. 181-187, Jun. 2004.

Parkes et al, "*Contribution of the IL-2 and IL-10 Genes to Inflammatory Bowel Disease (IBD) Susceptibility*", Clinical and Experimental Immunology, No. 113, pp. 28-32, 1998.

Tagore et al., "*Interleukin-10 (IL-10) Genotypes in Inflammatory Bowel Disease*", Tissue Antigens, No. 54, pp. 386-390, 1999.

Koss et al., "*Cytokine (TNFα, LTαand IL-10 Polymorphisms in Inflammatory Bowel Diseases and Normal controls: Differential Effects on Production and Allele Frequencies*", Genes and Immunity, No. 1, pp. 185-190, 2000.

Klein et al. "*The IL-10 Gene is not Involved in the Predisposition to Inflammatory Bowel Disease*", Electrophoresis, No. 21, pp. 3578-3582, 2000.

Aithal et al., "*Role of Polymorphisms in the Interleukin-10 Gene in Determining Disease Susceptibility and Phenotype in Inflamatory Bowel Disease*", Digestive Diseases and Sciences, vol. 46, No. 7, pp. 1520-1525, Jul. 2001.

Kim et al., "*Tumor Necrosis Factor-Alpha and Interleukin-10 Gene Polyntorphisms in Korean Patients with Inflammatory Bowel Disease*", Korean J. Gastroenterol, No. 42, pp. 377-386, 2003.

Celik et al., "*Cytokine Gene Polymorphisms in Turkish Patients with Inflammatory Bowel Disease*", Scandinavian Journal of Gastroenterology, No. 41, pp. 559-565, 2006.

Fernandez et al., "*Interleukin-10 Polymorphisms in Spanish Patients with IBD*", Inflammatory Bowel Disease, vol. 11, No. 8, pp. 739-743, Aug. 2005.

Cantor et al., "*The Role of Cytokine Gene Polymorphisms in Determining Disease Susceptibility and Phenotype in Inflammatory Bowel Disease*", American Journal of Gastroenterology, No. 100, pp. 1134-1142, 2005.

Castro-Santos et al., "*TNFαand IL-10 Gene Polymorphisms in Inflammatory Bowel Disease. Association of—1082 AA Low Producer IL-10 Genotype with Steroid Dependency*", American Journal of Gastroenterology, No. 101, pp. 1039-1047, 2006.

Trikalinos et al., "*Establishment of Genetic Associations for Complex Diseases is Independent of Early Study Findings*", European Journal of Human Genetics, No. 12, pp. 762-769, 2004.

Kolbe et al., "*Regulatory Potential Scores From Genome-Wide Three-Way Alignments of Human, Mouse, and Rat*", Genome Research, No. 14, pp. 700-707, 2004.

Hu et al., "*Crosstalk Among Jak-STAT, Toll-Like Receptor, and ITAM-Dependent Pathways in Macrophage Activation*", Journal of Leukocyte Biology, vol. 82, pp. 237-243, Aug. 2007.

Mitsuyama et al., "*Interleukin-10 in the Pathophysiology of Inflammatory Bowel Disease: Increased Serum Concentrations During the Recovery Phase*", Mediators of Inflammation, vol. 2006, Article ID 26875, pp. 1-7, 2006.

Schreiber et al., "*Immunoregulatory Role of Interleukin 10 in Patients with Inflammatory Bowel Disease*", Gastroenterology, No. 108, pp. 1434-1444, 1995.

Schreiber et al., "*Safety and Tolerance of rHuIL-10 Treatment in Patients with Mild/Moderate Active Ulcerative Colitis*", Gastroenterology, vol. 114, No. 4, pp. A1080-A1081,Apr. 1998.

Steidler et al., "*Treatment of Marine Colitis by Lactococcus Lactis Secreting Interieukin-10*", Science, vol. 289, pp. 1352-1355, Aug. 2000.

Franke et al., "*Genome- Wide Association Study for Ulcerative Colitis Demonstrates Novel Associations with IL17REL and 7q22*", Institute for Clinical Molecular Biology. 2009.

Paiss et al,"*Linkage of Aggressive Prostate Cancer to Chromosome 7q31-33 in German Prostate Cancer Families*", European Journal of Human Genetics, No. 11, pp. 17-22, 2003.

\* cited by examiner

SEQUENCE LISTING

<160> NUMBER OF SEQ ID NOS: 4

<210> SEQ ID NO 1
<211> LENGTH: 511
<212> TYPE: DNA
<213> ORGANISM: Homo sapiens

<400> SEQUENCE: 1

```
ctctttgagc tgagatcaga ggcaacaggg ctggacccaa cagagttgaa aataagcaaa      60
ttagcccact tgagaggata gccaaggaca taagctgctg ctctttctgt cccctctctg     120
agccaccaga caaatgtgag attggcttct gactgcggtc tgctgggagg ggcacggtgg     180
ctggggaagc cctactcaaa gccccgtgac ttagaggaga gaggaggaaa aaaatgagct     240
gagtaaacac tagtccccct cacgctctgc ctgggcagcc ctggtctggg aaggctggg      300
agcggacagg ctgtggtcag tttttcagta agacctgact cacttcggtt aaagtaacca     360
taggaaggaa gtgggaaaca tcaaagcgaa aattctgaga tgaaagggta ggagtaagaa     420
tggaggttag cagaagataa ggagagggg cctgaagctc tctactctga ggctgtccat      480
cctgaactga agaagacatc ctgagtctgt g                                    511
```

<210> SEQ ID NO 2
<211> LENGTH: 511
<212> TYPE: DNA
<213> ORGANISM: Homo sapiens

<400> SEQUENCE: 2

```
ctctttgagc tgagatcaga ggcaacaggg ctggacccaa cagagttgaa aataagcaaa      60
ttagcccact tgagaggata gccaaggaca taagctgctg ctctttctgt cccctctctg     120
agccaccaga caaatgtgag attggcttct gactgcggtc tgctgggagg ggcacggtgg     180
ctggggaagc cctactcaaa gccccgtgac ttagaggaga gaggaggaaa aaaatgagct     240
gagtaaacac tagtctccct cacgctctgc ctgggcagcc ctggtctggg aaggctggg      300
agcggacagg ctgtggtcag tttttcagta agacctgact cacttcggtt aaagtaacca     360
taggaaggaa gtgggaaaca tcaaagcgaa aattctgaga tgaaagggta ggagtaagaa     420
tggaggttag cagaagataa ggagagggg cctgaagctc tctactctga ggctgtccat      480
cctgaactga agaagacatc ctgagtctgt g                                    511
```

<210> SEQ ID NO 3
<211> LENGTH: 798
<212> TYPE: DNA
<213> ORGANISM: Homo sapiens
<220> FEATURE:
<221> NAME/KEY: misc_feature
<222> LOCATION: (1)..(91)
<223> OTHER INFORMATION: sequence identified by RepeatMasker as low-
      complexity or repetitive elements
<220> FEATURE:
<221> NAME/KEY: misc_feature
<222> LOCATION: (358)..(466)
<223> OTHER INFORMATION: sequence identified by RepeatMasker as low-
      complexity or repetitive elements

<400> SEQUENCE: 3

```
tgagttgggt cttgcaggat gaatagggat tttccagata gacctgggga aggaggcctg      60
tctaggcaca aagaacagca tgtgcaaagg cattgagcaa taacagagca atggaatcct     120
cagagttaac aggcagtttg tattatgagc aaccaggaa gtagacgagg ccagcaaggg      180
```

```
aggtaggaac caaatcatgc cctgtttgcc atgctacaag agtttggatt ttgcgctgca      240
gataaagaac caccagcata gtttaggaag atacttctac agcagaatgg ggctacactg      300
acaagagaga gacctgaagc aaggccagcc aggtactagt gctacccact gctcagaaga      360
attgcctggg gtacttgtta agtatacaga ttgcaaggcc ccctccagac ctgctgagtc      420
taggggaagg gcctgggaac ctatatgatt aacaggcatc ccaggttttc taacaaccaa      480
gaaaacacag agtgtaggag gttgcggcca ccatcctccg taggagaata aagggaaagg      540
gggaggggca tgttactgtg taattagggg aaggaatctg cataatgtgg tcaaagtgtt      600
gtgtgccagg gtgaggaaag cctggcatga ctgcgtagat agttgtacca tttaccaaga      660
cagggaatgc aagagaaaca gcaagtttag ggaaaataaa tcatgattta tttttgacaa      720
ggaattgatc aaaacgttgg ctctcaaagt gttgtcttgg caatgataaa aactattggt      780
ggtcgcagct cccagatg                                                   798

<210> SEQ ID NO 4
<211> LENGTH: 798
<212> TYPE: DNA
<213> ORGANISM: Homo sapiens
<220> FEATURE:
<221> NAME/KEY: misc_feature
<222> LOCATION: (1)..(91)
<223> OTHER INFORMATION: sequence identified by RepeatMasker as low-
      complexity or repetitive elements
<220> FEATURE:
<221> NAME/KEY: misc_feature
<222> LOCATION: (358)..(466)
<223> OTHER INFORMATION: sequence identified by RepeatMasker as low-
      complexity or repetitive elements

<400> SEQUENCE: 4
tgagttgggt cttgcaggat gaatagggat tttccagata gacctgggga aggaggcctg       60
tctaggcaca aagaacagca tgtgcaaagg cattgagcaa taacagagca atggaatcct      120
cagagttaac aggcagtttg tattatgagc aaccagggaa gtagacgagg ccagcaaggg      180
aggtaggaac caaatcatgc cctgtttgcc atgctacaag agtttggatt ttgcgctgca      240
gataaagaac caccagcata gtttaggaag atacttctac agcagaatgg ggctacactg      300
acaagagaga gacctgaagc aaggccagcc aggtactagt gctacccact gctcagaaga      360
attgcctggg gtacttgtta agtatacaga ttgcaaggcc ccctccagac ctgctgagtc      420
taggggaagg gcctgggaac ctatatgatt aacaggcatc ccaggttttc taacaaccaa      480
gaaaacacag agtgtaggag attgcggcca ccatcctccg taggagaata aagggaaagg      540
gggaggggca tgttactgtg taattagggg aaggaatctg cataatgtgg tcaaagtgtt      600
gtgtgccagg gtgaggaaag cctggcatga ctgcgtagat agttgtacca tttaccaaga      660
cagggaatgc aagagaaaca gcaagtttag ggaaaataaa tcatgattta tttttgacaa      720
ggaattgatc aaaacgttgg ctctcaaagt gttgtcttgg caatgataaa aactattggt      780
ggtcgcagct cccagatg                                                   798
```

METHOD FOR IDENTIFYING AN INCREASED SUSCEPTIBILITY TO ULCERATIVE COLITIS

CROSS-REFERENCE TO RELATED APPLICATIONS

This application represents a National Stage application of PCT/EP2008/008491 entitled "Method of Identifying an Increased Susceptibility to Ulcerative Colitis" filed Oct. 8, 2008, pending.

Inflammatory bowel disease (IBD) typically manifests as either ulcerative colitis (UC) or Crohn's disease (CD). Systematic identification of susceptibility genes for IBD has thus far focused mainly on CD, and little is known about the genetic architecture of UC.

The two main subtypes of inflammatory bowel disease (IBD), ulcerative colitis (UC, MIM191390) and Crohn's disease (CD, MIM266600), are chronic relapsing-remitting inflammatory disorders affecting the intestinal mucosa. Both diseases represent major burdens of morbidity in Western countries, with prevalence rates in North America and Europe ranging from 21 to 246 per 100,000 for UC and 8 to 214 per 100,000 for CD[1]. Although some clinical and pathological features are shared by these two subphenotypes of IBD, there are important differences in disease localization, endoscopic appearance, histology and behavior, which suggest differences in the underlying pathophysiology. In both diseases, inappropriate control of chronic inflammation has a major role[2].

The genetic contribution to disease risk has been documented more clearly for CD than for UC (relative sibling risks: 15-35 for CD, 6-9 for UC), and the recent identification of several CD susceptibility genes has yielded valuable insights into the pathogenesis of this IBD subtype[3]. In the clinical picture, some overlap is seen and the systematic analysis of CD risk markers shows that several of them are also associated with UC, including IL23R, IL12B, NKX2-3, CCNY and the 3p 21.31 (MST1) locus[4,5]. A genome-wide candidate gene experiment investigating 10,886 nonsynonymous SNPs in 1,470 British controls and 936 UC cases yielded ECM1 on 1q21.2 as a new UC-specific susceptibility gene[6]. However, a systematic, genomewide analysis of UC has not been reported so far.

Therefore, it has been an object of the invention to provide a method for identifying individuals having a nucleic acid molecule associated with Ulcerative Colitis, which might account for an increased susceptibility to Ulcerative Colitis resulting from the presence of a polymorphism.

TABLE 1

Summary of association results of replication

| Position (bp) | dbSNP ID | A1 A2 | Panel A - GWAS 777 controls/1,167 UC cases | | | Panel B - Germany 985 controls, 523 UC cases | | | Panel C - UK 1,091 controls, 304 UC cases | | |
|---|---|---|---|---|---|---|---|---|---|---|---|
| | | | $AF_{A1}$ Con. Case | $P_{CCA}$ | OR (95% CI) | $AF_{A1}$ Con. Case | $P_{CCA}$ | OR (95% CI) | $AF_{A1}$ Con. Case | $P_{CCA}$ | OR (95% CI) |
| 6p21.32 HLA-DRA (32,539,125) | rs9268877 | T C | 0.44 0.52 | 5.23E−7 | 1.51 (1.23-1.86) | 0.44 0.54 | 5.68E−8 | 1.91 (1.48-2.46) | 0.40 0.50 | 9.94E−6 | 1.87 (1.39-2.49) |
| 6p21.32 HLA-DRA (32,537,736) | rs9268858 | G A | 0.30 0.22 | 5.41E−7 | 0.65 (0.54-0.78) | 0.29 0.22 | 1.27E−5 | 0.67 (0.54-0.83) | 0.37 0.31 | 0.0067 | 0.86 (0.67-1.12) |
| 6p21.33 BTNL2 (32,471,822) | rs9268480 | A G | 0.27 0.20 | 2.21E−6 | 0.62 (0.52-0.75) | 0.27 0.21 | 4.00E−4 | 0.67 (0.54-0.84) | 0.31 0.25 | 0.0076 | 0.72 (0.56-0.93) |
| 1p31.2 IL23R (67,387,537) | rs11805303 | T C | 0.26 0.33 | 5.39E−6 | 1.50 (1.25-1.80) | 0.27 0.32 | 0.0057 | 1.39 (1.12-1.72) | 0.31 0.36 | 0.019 | 1.20 (0.92-1.55) |
| 2q35 ARPC2 (218,882,844) | rs12612347 | T C | 0.45 0.52 | 8.42E−6 | 1.60 (1.30-1.96) | 0.49 0.52 | 0.14 | 1.22 (0.94-1.57) | 0.48 0.54 | 0.0098 | 1.37 (1.01-1.86) |
| 1q32.1 IL10 (203,328,299) | rs3024505 | T C | 0.14 0.20 | 1.43E−5 | 1.52 (1.24-1.85) | 0.16 0.21 | 0.0012 | 1.48 (1.18-1.86) | 0.14 0.21 | 3.51E−5 | 1.64 (1.25-2.15) |
| 3p12.1 CADM2 (85,842,248) | rs7611991 | A G | 0.29 0.23 | 6.15E−5 | 0.71 (0.60-0.86) | 0.25 0.22 | 0.034 | 0.75 (0.60-0.93) | 0.26 0.25 | 0.76 | 0.98 (0.76-1.27) |
| 9p24.1 JAK2 (5,060,831) | rs10974944 | G C | 0.25 0.31 | 7.95E−5 | 1.42 (1.18-1.70) | 0.30 0.31 | 0.69 | 1.01 (0.82-1.26) | 0.27 0.26 | 0.58 | 0.89 (0.69-1.15) |
| 5q13.3 S100Z (76,174,452) | rs7712957 | G A | 0.07 0.11 | 8.98E−5 | 1.61 (1.26-2.06) | 0.08 0.09 | 0.63 | 1.04 (0.78-1.40) | 0.10 0.11 | 0.45 | 1.15 (0.84-1.57) |

| Position (bp) | dbSNP ID | A1 A2 | Panel D - Belgium/Netherlands 1,015 controls, 1,028 UC cases | | | Combined analysis (panels B-D) 3,091 controls, 1,855 UC cases | |
|---|---|---|---|---|---|---|---|
| | | | $AF_{A1}$ Con. Case | $P_{CCA}$ | OR (95% CI) | $P_{BD}$ | $P_{CMH}$ OR (95% CI) |
| 6p21.32 HLA-DRA (32,539,125) | rs9268877 | T C | 0.45 0.53 | 3.10E−7 | 1.14 (0.94-1.38) | 0.61 | 6.48E−18[a] 1.45 (1.33-1.58) |
| 6p21.32 HLA-DRA (32,537,736) | rs9268858 | G A | 0.27 0.20 | 1.20E−6 | 0.63 (0.53-0.76) | 0.61 | 2.58E−12[a] 0.71 (0.64-0.78) |

TABLE 1-continued

Summary of association results of replication

| Location | SNP | Allele | Freq | P (panel A) | OR (panel A) | P (combined) | OR (combined) |
|---|---|---|---|---|---|---|---|
| 6p21.33 BTNL2 (32,471,822) | rs9268480 | A G | 0.25 0.20 | 1.21E-4 | 0.67 (0.56-0.80) | 0.95 | 3.15E-9[a] 0.74 (0.67-0.82) |
| 1p31.2 IL23R (67,387,537) | rs11805303 | T C | 0.28 0.32 | 0.011 | 1.26 (1.05-1.50) | 0.86 | 1.09E-5[a] 1.23 (1.12-1.35) |
| 2q35 ARPC2 (218,882,844) | rs12612347 | T C | 0.46 0.50 | 0.013 | 1.23 (1.00-1.50) | 0.59 | 2.00E-4[b] 1.18 (1.08-1.28) |
| 1q32.1 IL10 (203,328,299) | rs3024505 | T C | 0.15 0.21 | 8.04E-6 | 1.50 (1.24-1.81) | 0.75[b] | 1.35E-12[a, b] 1.46 (1.31-1.62)[b] |
| 3p12.1 CADM2 (85,842,248) | rs7611991 | A G | 0.27 0.25 | 0.14 | 0.91 (0.76-1.09) | 0.49 | 0.023 0.89 (0.81-0.98) |
| 9p24.1 JAK2 (5,060,831) | rs10974944 | G C | 0.26 0.31 | 6.98E-4 | 1.30 (1.09-1.55) | 0.036 | 0.023 1.12 (1.02-1.23) |
| 5q13.3 S100Z (76,174,452) | rs7712957 | G A | 0.09 0.11 | 0.042 | 1.21 (0.96-1.52) | 0.64 | 0.039 1.16 (1.01-1.34) |

We set out to identify UC susceptibility loci systematically in a large sample of 1,167 cases and 777 healthy controls (panel A, Table 1) by testing 440,794 SNPs with the Affymetrix SNP Array 5.0 (Supplementary Methods). Screening panel A had 80% power to detect a variant with an odds ratio of 1.5 or higher at the 5% significance level, assuming a frequency of the disease-associated allele of at least 20% in controls. Genotyping was done blind to case-control status, and several HapMap samples with known genotype were included in each batch for quality control. After applying stringent quality control criteria (Supplementary Methods) to the genotype data from panel A, we included all 1,944 samples and a subset of 355,262 SNPs in the final association analysis. The total genotyping rate across these samples was 99.8%. We found genetic heterogeneity to be low, with an estimated genomic inflation factor[7] of 1GC=1.11. P values with and without correction for structure were similar and consequently, unadjusted P values are shown below. We genotyped the 20 most strongly associated SNPs that passed selection criteria for replication (Supplementary Methods) in three additional panels of UC cases and healthy controls (panels B, C and D in Table 1, see also Supplementary Methods). The results of the association analysis are summarized in Table 1.

New associations that withstood correction for multiple testing using Bonferroni correction (a=0.0025 (0.05/20)) across all three replication panels were obtained for rs3024505 near the 3' UTR of the ILI10 gene at 1q32, for rs12612347 near the ARP2C locus at 2q35 and for rs9268480, rs9268858 and rs9268877 at the class II-class III junction in the HLA complex at 6p 21 (Table 1). The findings at the latter three SNPs, located near the HLA class II genes on chromosome 6p 21, are not surprising given the large body of evidence for an association between classical HLA loci and UC[8]. Because of the complex pattern of linkage disequilibrium (LD) in this region, comprehensive experiments beyond the scope of the present study will be required to clarify whether the observed associations are due to variation in the HLA class II genes themselves, at neighbouring loci (for example, BTNL2), or both. Another notable finding in the present study is the consistent association between ARPC2 and UC. The exact function of ARPC2 is not known. The microbial equivalent of human Arp2/3 associates with the protein encoded by the WAS gene, which, when mutated in humans, causes Wiskott-Aldrich syndrome (WAS). Notably, the WAS protein is involved in the regulation of regulatory T cells[9], and manifestation of UC has been reported as the first sign of disease in an individual with WAS[10]. Genome-wide linkage studies have also provided evidence for UC susceptibility factors in the respective region at 2q[11]. That the previously reported IL23R association4 replicated in all sample panels of the present study (SNP rs11805303: combined P=1.09*10$^{-5}$ and OR=1.23 (1.12-1.35)), albeit at lower levels of significance than IL10, highlights a role for this locus in UC as well as CD. Population attributable risk fractions (%) in the combined panel (B-D) were 12.7, 13.3, 42.6, 47.8, 32.1 and 9.8 for SNPs rs3024505, rs12612347, rs9268480, rs9268858, rs9268877 and rs11805303, respectively (Supplementary Methods).

Figure 1:
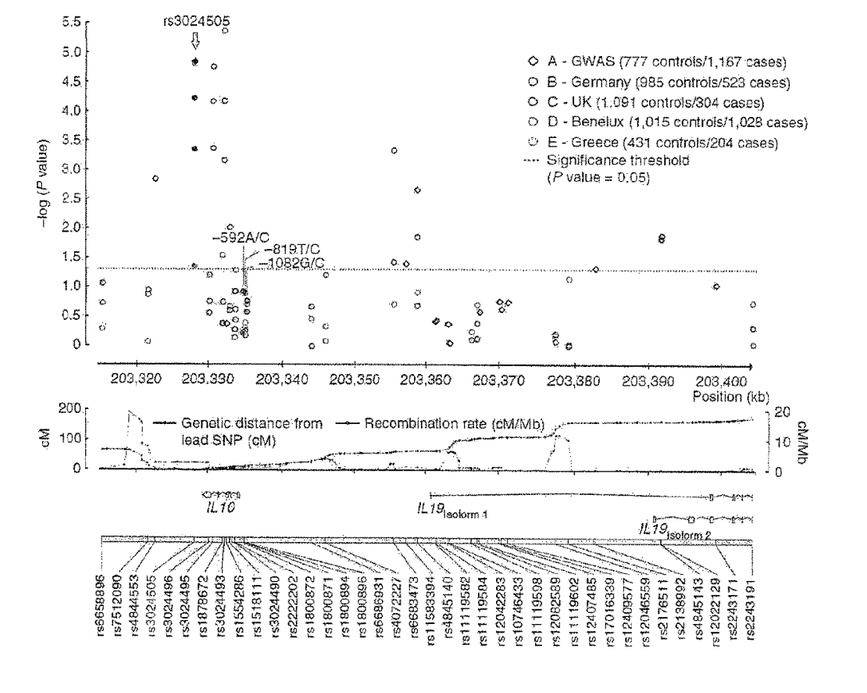

In the combined analysis, the most significant association outside the HLA complex in the replication analysis was obtained for rs3024505 located 1 kb downstream of the 3 UTR of IL10 (P=1.35*10$^{-12}$; OR=1.46 (1.31-1.62)). In a consecutive analysis we did not find strong evidence for an association between rs3024505 and the CD phenotype (P=0.013; OR 1.17 (1.01-1.34)) in 1,804 healthy controls and 1,848 CD cases. We saturated the IL10 locus using an additional 22 HapMap tagging SNPs in an attempt to narrow down the association signal and to support the disease association of the lead SNP. All fine mapping SNPs were genotyped in the UC replication panels B to D, revealing associations that included rs3024495 in intron 4 (P=2.69*10$^{-11}$ in combined analysis) and rs3024493 in intron 3 (P=6.16*10$^{-12}$ in combined analysis), together with lead SNP rs3024505 (FIG. 1). The risk alleles of these three SNPs were in perfect LD with each other ($r^2$=1.00), but not with any of the other 20 SNPs used for fine mapping ($r^2 \leq 0.20$). In a logistic regression analysis of the combined panels B-D, applying forward selection to the 23 fine-mapping SNPs, we achieved the best model fit for SNPs rs3024496 (3' UTR), rs6658896 (14 kb 3' of IL10) and rs4845140 (25 kb 5' of IL10), in addition to lead SNP rs3024505, suggesting that more than one causal variant might contribute to the association signal at the IL10 locus. A haplotype analysis of the latter four SNPs supported this finding.

FIG. 1 shows a regional plot of the confirmed UC association at IL10. Plot of the negative decadic logarithm of the P values obtained in the GWAS (panel A) and the fine mapping in replication panels B to E. Twenty-three tagging SNPs, including lead SNP rs3024505 (highlighted by filled symbols), were genotyped across the 89-kb region surrounding the IL10 gene. The three IL10 promoter SNPs rs1800872 (-C592A), rs1800871 (-C819T) and rs1800896 (-G1082A) are highlighted. Nominal P values for each UC case-control panel are shown and are based on a Pearson w2 test with one degree of freedom. The red dotted line corresponds to a threshold of 0.05 for the P value. The middle panel includes plots of the recombination intensity (cM/Mb) and the cumulative genetic distance in cM, and the bottom panel shows the position and intron-exon structure of IL10 and part of the upstream IL19 gene. Positions are given as NCBI build 35 coordinates.

These data taken together clearly identified IL10 as a susceptibility gene for UC, but the causative variant(s) within the gene remained to be found. We resequenced the entire IL10 gene—that is, the promoter, introns and exons—in 94 individuals with UC, 94 individuals with CD and 94 healthy controls. In total, we identified 25 known SNPs and 19 additional SNPs, all of which were private or rare variants. No indel polymorphism was identified. Two private nonsynonymous SNPs not previously described (encoding F129Y and R177Q) were detected alongside a rare synonymous SNP (K135K) and the previously identified G15R variant, which has failed to show significant association with CD in previous studies[12]. Our results corroborate this finding and extend the association to UC, as only one heterozygote sample was found among the 282 samples that were resequenced.

Three key observations can be made regarding the possible causality of the variants identified by the present fine mapping and association analysis. First, we did not find any evidence of a UC association for any of the previously investigated SNPs at IL10 promoter positions −592 (rs1800872), −819 (rs1800871) and −1082 (rs1800896)[13-23]. Only two out of as many as ten previous studies have so far yielded evidence for an association of UC with the SNPs at these positions[15,21], That eight of these previous studies have been unable to generate evidence for an IL10 association in UC highlights general limitations of study design and statistical power in a large fraction of historical candidate gene studies24. The variable evidence for the association detected between the promoter SNPs and UC is probably due to different levels of LD between the promoter SNPs and the main SNP responsible for the association signal which, according to our data, is likely to reside elsewhere at the IL10 locus. Second, the close proximity (79 bp) of lead SNP rs3024505 to a highly conserved stretch of DNA at the 3' end of the gene is of interest. This region has a high regulatory potential score25 and contains a putative AP-1 binding motif. AP-1 is activated upon stimulation of macrophages by the bacterial cell-wall component lipopolysaccharide[26], and IL10 production could provide an important anti-inflammatory feedback mechanism. Finally, we carried out an extensive analysis of the influence of the two newly identified exonic variants on the interaction sites between IL10 and the high-affinity IL10 receptor A (IL10RA). To what extent carriage of either of these variants can be functionally linked to UC susceptibility in the individuals in question can, however, only be speculated.

Our findings clearly suggest that IL10 may be a key cytokine in UC pathogenesis. This hypothesis is strongly supported by the spontaneous colitis phenotype developed by $Il10^{-/-}$ mice, which seems to result from a defective anti-inflammatory counter-regulation in response to the commensal flora. Notably, a reduced IL10 in vitro regulation in inflammatory immune cells obtained from the mucosa of individuals of UC has been described, and therapeutic administration of human recombinant IL10 to individuals with UC had a positive clinical effect[27-29]. Subcutaneous administration of IL10 was not further evaluated as a therapeutic in UC after failing in clinical studies of CD. In light of these results, systemic or topical delivery of IL10 should be worthy of consideration for clinical trials in UC. As a delivery mechanism, genetically engineered IL10-secreting Lactococcus lactic strains have been developed as a potent tool to influence colonic mucosal immunoregulation[30]. A role of IL10 has also been suggested in other forms of chronic inflammation, for example rheumatoid arthritis, lupus erythematosus and psoriasis, and it should be worthwhile to investigate the IL10 locus by a haplotype-tagging approach in these conditions.

IL10 signals through STAT3- and MAPK-mediated pathways to trigger anti-inflammatory mechanisms dependent on suppressor of cytokine signaling[26]. Recently, a targeted assessment of CD susceptibility genes for their role in UC revealed an association between a SNP in STAT3 and UC[5]. SNP rs744166, located in intron 2 of STAT3 at 17q21.2, which had been associated with CD in the Wellcome Trust Case Control Consortium (WTCCC) genome-wide association study[7], proved to be associated with UC in that study (OR=0.77 (0.66-0.90), P=5.00*$10^{-4}$), but not with CD. In this context, it is of great interest to note retrospectively that SNP rs7212299, located upstream of STAT3, was also found to be associated with UC in the present study (panel A). Because of the low level of significance (P=0.01) the SNP was, however, not included in the replication phase of this study. We anticipate that further characterization of critical components of the IL10-STAT3 signaling pathway may point to important therapeutic targets and provide unique insights into the pathogenesis of UC.

Herewith we have reported a genome-wide association study with 440,794 SNPs genotyped in 1,167 individuals with UC and 777 healthy controls. Twenty of the most significantly associated SNPs were tested for replication in three independent European case-control panels comprising a total of 1,855 individuals with UC and 3,091 controls. Among the four consistently replicated markers, SNP rs3024505 immediately flanking the IL10 (interleukin 10) gene on chromosome 1q32.1 showed the most significant association in the combined verification samples (P=1.35*$10^{-12}$; OR=1.46 (1.31-1.62)). The other markers were located in ARPC2 and in the HLA-BTNL2 region. Association between rs3024505 and CD (1,848 cases, 1,804 controls) was weak (P=0.013; OR=1.17 (1.01-1.34)). IL10 is an immunosuppressive cytokine that has long been proposed to influence IBD pathophysiology. Our findings strongly suggest that defective IL10 function is central to the pathogenesis of the UC subtype of IBD.

Methods

Participants. The diagnosis of UC or CD was based on typical clinical, radiological, histological and endoscopic (type and distribution of lesions) findings. The full recruitment details for all study panels are given in Supplementary Methods. All participants gave written informed consent, and the recruitment protocols were approved by the ethics committees at the respective recruiting institutions.

Genotyping and sequencing. The genotyping for the GWAS was performed as a service project by Affymetrix using the Genome-Wide Human SNP Array 5.0 (500K). Genotypes were assigned using the BRLMM-p algorithm. Samples with more than 5% missing genotypes, who showed excess genetic dissimilarity to the other subjects, or who showed evidence for cryptic relatedness to other study participants were not included. These quality control measures left 1,167 UC samples and 777 control samples for inclusion in screening panel A, SNPs were excluded (n=85,532; 19.4% of all SNPs) that had a low genotyping rate (<95% in cases or controls), were monomorphic or rare (minor allele frequency<2% in cases or controls), or deviated from Hardy-Weinberg equilibrium (HWE) in the control sample (PHWE≤0.01).

All downstream genotyping was done with SNPlex and TaqMan technologies (Applied Biosystems) using an automated laboratory setup and all process data were written to and administered by a database-driven laboratory information management system. Sequencing of genomic DNA was done using BigDye Terminator v3.1 chemistry (Applied Biosystems) and an ABI3730 capillary sequencer (Applied Biosystems) according to manufacturer's protocols. Traces were inspected for SNPs and indels using novoSNP v2.03. See Supplementary Methods for further details.

Statistical analysis. Genome-wide association analyses were conducted with PLINK v 1.01 in combination with gPLINK v2.049 and GENOMIZER v1.2.0. Single-marker analyses, permutation tests, estimation of pair-wise linkage disequilibrium (LD) and SNP selection were done using Haploview v4.0. Logistic regressions were done within LOGISTIC of the SAS software package (SAS Institute). For additional details, see Supplementary Methods.

Here we report a genome-wide association study with 440,794 SNPs genotyped in 1,167 individuals with UC and 777 healthy controls. Twenty of the most significantly associated SNPs were tested for replication in three independent European case-control panels comprising a total of 1,855 individuals with UC and 3,091 controls. Among the four consistently replicated markers, SNP rs3024505 immediately flanking the IL10 (interleukin 10) gene on chromosome 1q32.1 showed the most significant association in the combined verification samples (P=1.35*10$^{-12}$; OR=1.46 (1.31–1.62)). The other markers were located in ARPC2 and in the HLA-BTNL2 region. Association between rs3024505 and CD (1,848 cases, 1,804 controls) was weak (P=0.013; OR=1.17 (1.01–1.34)). IL10 is an immunosuppressive cytokine that has long been proposed to influence IBD pathophysiology. Our findings strongly suggest that defective IL10 function is central to the pathogenesis of the UC subtype of IBD.

The method according to the invention is based on the finding that there is an increased susceptibility to ulcerative colitis due to the presence of a polymorphism at position 256 of the nucleotide sequence of rs3024505 (SEQ ID NO:1) in which C is substituted by T (cf. SEQ ID NO: 2) or the presence of a polymorphism at position 501 of the nucleotide sequence of rs12612347 (SEQ ID NO: 3) in which G is substituted by A (cf. SEQ ID NO: 4). Therefore, individuals with or without increased susceptibility can be identified.

Further, the invention provides the use of a vector comprising a nucleotide sequence of SEQ ID NO: 1 or SEQ ID NO: 3 for preparing a pharmaceutical composition for the treatment of ulcerative colitis by means of gene therapy.

LITERATURE

Incorporated Herein by Reference

1. Loftus, E. V. Jr. Clinical epidemiology of inflammatory bowel disease: incidence, prevalence, and environmental influences. Gastroenterology 126, 1504-1517 (2004).
2. Bouma, G. & Strober, W. The immunological and genetic basis of inflammatory bowel disease. Nat. Rev. Immunol. 3, 521-533 (2003).
3. Mathew, C. G. New links to the pathogenesis of Crohn disease provided by genome-wide association scans. Nat. Rev. Genet. 9, 9-14 (2008).
4. Duerr, R. H. et al. A genome-wide association study identifies IL23R as an inflammatory bowel disease gene. Science 314, 1461-1463 (2006).
5. Franke, A. et al. Replication of signals from recent studies of Crohn's disease identifies previously unknown disease loci for ulcerative colitis. Nat. Genet. 40, 713-715 (2008).
6. Fisher, S. A. et al. Genetic determinants of ulcerative colitis include the ECM1 locus and five loci implicated in Crohn's disease. Nat. Genet. 40, 710-712 (2008).
7. Devlin, B. & Roeder, K. Genomic control for association studies. Biometrics 55, 997-1004 (1999).
8. Stokkers, P. C., Reitsma, P. H., Tytgat, G. N. & van Deventer, S. J. HLA-DR and -DQ phenotypes in inflammatory bowel disease: a meta-analysis. Gut 45, 395-401 (1999).
9. Marangoni, F. et al. WASP regulates suppressor activity of human and murine CD4(+) CD25(+) FOXP3(±) natural regulatory T cells. J. Exp. Med. 204, 369-380 (2007).
10. Webb, M. C., Andrews, P. A., Koffman, C. G. & Cameron, J. S. Renal transplantation in Wiskott-Aldrich syndrome. Transplantation 56, 1585 (1993).
11. van Heel, D. A. et al. Inflammatory bowel disease susceptibility loci defined by genome scan meta-analysis of 1952 affected relative pairs. Hum. Mol. Genet. 13, 763-770 (2004).
12. van der Linde, K. et al. A functional interleukin-10 mutation in Dutch patients with Crohn's disease. Dig. Liver Dis. 37, 330-335 (2005).
13. Balding, J. et al. Inflammatory bowel disease: the role of inflammatory cytokine gene polymorphisms. Mediators Inflamm. 13, 181-187 (2004).
14. Parkes, M., Satsangi, J. & Jewell, D. Contribution of the IL-2 and IL-10 genes to inflammatory bowel disease (IBD) susceptibility. Clin. Exp. Immunol. 113, 28-32 (1998).
15. Tagore, A. et al. Interleukin-10 (IL-10) genotypes in inflammatory bowel disease. Tissue Antigens 54, 386-390 (1999).
16. Koss, K., Satsangi, J., Fanning, G. C., Welsh, K. I. & Jewell, D. P. Cytokine (TNF alpha, LT alpha and IL-10) polymorphisms in inflammatory bowel diseases and normal controls: differential effects on production and allele frequencies. Genes Immun. 1, 185-190 (2000).
17. Klein, W. et al. The IL-10 gene is not involved in the predisposition to inflammatory bowel disease. Electrophoresis 21, 3578-3582 (2000).
18. Aithal, G. P. et al. Role of polymorphisms in the interleukin-10 gene in determining disease susceptibility and phenotype in inflamatory bowel disease. Dig. Dis. Sci. 46, 1520-1525 (2001).
19. Kim, T. H. et al. Tumor necrosis factor-alpha and interleukin-10 gene polymorphisms in Korean patients with inflammatory bowel disease. Korean J. Gastroenterol. 42, 377-386 (2003).
20. Celik, Y. et al. Cytokine gene polymorphisms in Turkish patients with inflammatory bowel disease. Scand. J. Gastroenterol. 41, 559-565 (2006).
21, Fernandez, L. et al. Interleukin-10 polymorphisms in Spanish patients with IBD. Inflamm. Bowel Dis. 11, 739-743 (2005).
22. Cantor, M. J., Nickerson, P. & Bernstein, C. N. The role of cytokine gene polymorphisms in determining disease susceptibility and phenotype in inflammatory bowel disease. Am. J. Gastroenterol. 100, 1134-1142 (2005).
23. Castro-Santos, P., Suarez, A., Lopez-Rivas, L., Mozo, L. & Gutierrez, C. TNFalpha and IL-10 gene polymorphisms in inflammatory bowel disease. Association of –1082 AA low producer IL-10 genotype with steroid dependency. Am. J. Gastroenterol. 101, 1039-1047 (2006).

24. Trikalinos, T. A., Ntzani, E. E., Contopoulos-Ioannidis, D. G. & Ioannidis, J. P. Establishment of genetic associations for complex diseases is independent of early study findings. Eur. J. Hum. Genet. 12, 762-769 (2004).
25. Kolbe, D. et al. Regulatory potential scores from genome-wide three-way alignments of human, mouse, and rat. Genome Res. 14, 700-707 (2004).
26. Hu, X., Chen, J., Wang, L. & Ivashkiv, L. B. Crosstalk among Jak-STAT, Toll-like receptor, and ITAM-dependent pathways in macrophage activation. J. Leukoc. Biol. 82, 237-243 (2007).
27. Mitsuyama, K. et al. Interleukin-10 in the pathophysiology of inflammatory bowel disease: increased serum concentrations during the recovery phase. Mediators Inflamm. 2006, 26875 (2006).
28. Schreiber, S., Heinig, T., Thiele, H. G. & Raedler, A. Immunoregulatory role of interleukin 10 in patients with inflammatory bowel disease. Gastroenterology 108, 1434-1444 (1995).
29. Schreiber, S. et al. Ulcerative Colitis IL-10 Cooperative Study Grp T1 Safety and tolerance of rHuIL-10 treatment in patients with mild/moderate active ulcerative colitis. Gastroenterology 114, A1080-A1081 (1998).
30. Steidler, L. et al. Treatment of murine colitis by Lactococcus lactis secreting interleukin-10. Science 289, 1352-1355 (2000).

Supplementary Methods & Materials
Overview of Case-Control Samples

Samples were organized in panels that corresponded to the successive steps of the present study. All panels were independent from each other, except for the control samples of panel. F which included all control samples of panel B.

| Panel | Controls | Cases |
|---|---|---|
| A - UC GWAS panel (Germany/Norway) | 777 | 1167 |
| B - UC validation panel 1 (Germany) | 985 | 523 |
| C - UC replication panel 2 (UK) | 1091 | 304 |
| D - UC replication panel 3 (Benelux) (Belgium/Netherlands) | 1015 (364/651) | 1028 (451/577) |
| E - UC replication panel 5 (Greece) | 431 | 204 |
| F - CD (Germany) | 1804 | 1848 |

Recruitment of Patients and Healthy Controls

German patients of panels A (874 out of 1167 total), B, and F (see Table above) were recruited either at the Department of General Internal Medicine of the Christian-Albrechts-University Kiel, the Charité University Hospital Berlin, through local outpatient services, or nationwide with the support of the German Crohn and Colitis Foundation. Clinical, radiological, histological, and endoscopic (i.e. type and distribution of lesions) examinations were required to unequivocally confirm the diagnosis of ulcerative colitis (UC) or Crohn disease (CD)[1,2].

479 German healthy control individuals of panel A (777 total) were obtained from the popgen biobank[3]. Written, informed consent was obtained from all study participants and all protocols were approved by the institutional ethical review committees of the participating centres. Patients and controls overlapped to a small extent with samples that have been used in previous studies[4-8].

The 293 clinically well-characterised Norwegian UC patients of panel A (total 1167) were recruited through a population-based incidence study, the Inflammatory Bowel disease in South-Eastern Norway (IBSEN) study[9,10].

An ethnically and sex-matched group of Norwegian healthy controls (n=298 of 777 total of panel A) was randomly selected from the Norwegian Bone Marrow Donor Registry (NBMDR). The strict criteria (including absence of any autoimmune disease) on inclusion in the NBMDR ensured correct classification of these controls as healthy.

The UK study population of panel C were recruited as described previously[11]. UK healthy controls of panel C were obtained from the 1958 British Birth Cohort (1958 BC; http://www.b58cgene.sguLac.uk). This control panel was a perfect subset of the 1.958 BC samples used in the WTCCC study[12].

The Benelux study population (panel D) consisted of 1028 UC patients of Caucasian ethnicity from the IBD unit of the University Hospital in Leuven, Belgium (n=451), the Academic Medical Center, Amsterdam (n=367) and the University Medical Center Groningen, the Netherlands (n=210) and has been used and described in various previous publications[13-15]. A significant overlap exists between the patient panel of the study by Dideberg et al. 16 and the samples included in Panel D of the present study (n=248 samples from Leuven used by Dideberg et al., and n=181 of these cases were included amongst the 451 Belgian samples in Panel D of the present study). The healthy controls of panel D consisted of 1015 healthy Caucasian volunteers from the University Medical Center Utrecht, the Netherlands (n=651) and the University Hospital in Leuven, Belgium (n=364).

The Greek study population (panel E) consisted of 206 UC cases, and 150 age- and sexmatched healthy controls (blood donors). Part of this panel has been used in previous studies[17,18]. None of the patients or controls had a family history of autoimmune disease. The diagnosis of UC was based on standard clinical, endoscopic, radiological, and histological criteria. Before commencement of the study, the Ethics Committee at the participating centers approved the recruitment protocols. All participants were informed of the study. DNA was isolated from blood with the NucleoSpin blood kit (Macherey-Nagel, Germany).

To account for their heterogeneous sources, all DNA samples were first evaluated by gel electrophoresis.

SNP Genotyping of Genome-Wide Screen

The Genotyping for the GWAS—which was part of the German NGFN GWAS initiative (see press release 04-26-07 on http://www.ngfn.de/englisch/index_368.htm) funded by the NGFN—was performed by an Affymetrix service facility (South San Francisco, Calif., USA) using the Affymetrix Genome-Wide Human SNP Array 5.0 (500 k) (Santa Clara, Calif., USA). The array is based on an assay termed whole-genome sampling analysis (WGSA) developed for highly multiplexed SNP genotyping of complex DNA. This method reproducibly amplifies a subset of the human genome through a single primer amplification reaction using restriction enzyme digested, adapter-ligated human genomic DNA.

In brief, 5 µl of genomic DNA samples at 50 ng/ul were aliquoted to the corresponding wells of two 96-well plates. The first run of samples was processed as an entire plate. In the lab, transfers were made with a 12-channel pipette, reducing the risk of sample tracking errors. One plate was digested with Nsp I and the other plate was digested with Sty I. The reaction was incubated at 37° C. for 2 hours and at 65° C. for 20 minutes to deactivate the enzyme. The digested DNA was then ligated to their respective Nsp I adaptor and Sty I adaptor. The ligated product was then PCR-amplified using a common primer. Both Nsp I PCR product and Sty I PCR product were combined, and then purified by ethanol precipitation in combination with membrane filter plate. Purified PCR product was further fragmented with DNase I then labeled with biotin. Labeled DNA was combined with hybridization mix and then injected into array. Arrays were hybridized for 18 to 22 hours at 50° C. DNA samples were recovered from arrays and washed and stained by using Affymetrix FS450 fluidic stations. Stained arrays were scanned using Affymetrix GeneChip Scanner 3000 7G.

Raw image files were converted into .cel-files by Affymetrix genotyping console. A preliminary QC call rate of 86% was used to pass arrays for further data analysis. Passed arrays were clustered in the same batches which were processed together in the lab.

Genotypes were assigned using the BRLMM-p algorithm. More than 95% of samples processed by Affymetrix net the 86% QC call rate (CR) and 97% BRLMM-p call rate specification, respectively. There were 12 positive control samples run in each project. The positive controls were from a CEPH trio family: NA12740—daughter (6 repeats), NA12750—father (4 repeats), and NA 12751—mother (4 repeats). This set of controls allowed to calculate experimental reproducibility, trio accuracy, and HapMap concordance. The performance metrics were as follows (supplied by Affymetrix service facility):

| | |
|---|---|
| Average QC call rate | >96.50% |
| Average BRLMM-P call rate | >99.50% |
| Average Reproducibility (controls) | >99.90% |
| Average HAPMAP Concordance (controls) | >99.50% |
| Average Trio Accuracy (controls) | >99.90% |

Although these benchmarks suggest an accurate genotype assignment of the raw intensity data, there is still room for improvement regarding the development of novel calling algorithms as pointed out by other groups as well 12. Samples with more than 5% missing genotypes, who showed excess genetic dissimilarity to the other subjects (see FIG. S3), or who showed evidence for cryptic relatedness to other study participants (see FIG. S3) were removed. These quality control measures left 1167 UC samples and 777 control samples for inclusion in screening panel A. All gender assignments could be verified by reference to the proportion of heterozygous SNPs on the X chromosome. SNPs were excluded (n=85,532; 19.4% of all SNPs) that had a low genotyping rate (<95% in cases or controls), were monomorphic/rare (minor allele frequency<2% in cases or controls), or deviated from Hardy-Weinberg equilibrium (HWE) in the control sample (PHWE≤0.01). The number of excluded SNPs is in line with that of other published Affymetrix 500 k GWAS[12,19].

SNPlex and TaqMan Genotyping

For replication and fine mapping of the IL10 gene region, ligation-based SNPlex™ genotyping (Applied Biosystems, Foster City, Calif., USA) was performed in panels B to D as described previously 6. Genotype assignments were verified visually using the Genemapper 4.0 (Applied Biosystems) software. For fine mapping of IL10, twenty-three SNPs, including lead SNP rs3024505, were selected from the HapMap dataset of Utah residents with ancestry from northern and western Europe (CEU; minor allele frequency>1%, pairwise r2 between tagged. SNPs>0.8, PHWE>0.05, <3 Mendelian errors) using de Bakker's tagging algorithm[20] as implemented in Haploview 21. Functionally tested TaqMan® SNP Genotyping Assays (Applied Biosystems) were used to genotype the three promoter SNPs rs1800896 (C__1747360__10; −1082), rs1800872 (C_1747363__10; −592), rs1800871 (C__1747362__10; −819), and the lead SNP rs3024505 (C__15983681__20) in panels B-D and F. The latter SNP was genotyped for technical validation using an independent genotyping method. The resulting concordance rate for SNP rs3024505 in panels B-G was >98%, excluding genotyping errors as a potential source of false-positive associations. All process data were written to, and administered by a previously described database-driven laboratory information management system (LIMS) 22. Duplicate or related samples were identified and excluded from the analyses, using algorithms implemented in the LIMS. However, no specific genotyping was conducted to "ID" tag the DNA samples.

All SNPs had a high call rate (>90% in cases or controls), were not monomorphic (minor allele frequency<1% in cases or controls), and did not deviate from Hardy-Weinberg equilibrium (HWE) in the control population (PHWE>0.01).

Statistical Analyses

Power calculations were carried out using PS Power and Sample Size v2.130 23. GWAS data were analysed using gPLINK v2.049 in combination with PLINK v1.01 24 and GENOMIZER v1.2.0 25. The clump command was used to reduce the number of SNPs for follow-up by removing correlated hit SNPs. To this end, the following thresholds were applied:

clump-p1 0.0001 Significance threshold for index SNPs
clump-p2 0.01 Secondary significance threshold for clumped SNPs
clump-r2 0.50 LD threshold for clumping
clump-kb 250 Physical distance threshold for clumping Single-marker association analyses, permutation tests, estimation of pair-wise linkage disequilibrium (LD), and SNP selection were performed using Haploview 4.0 21. Single-marker disease associations and possible marker-marker interactions were assessed for statistical significance by means of logistic regression analysis (forward selection), as implemented in the procedure LOGISTIC of the SAS software package (SAS Institute, Cary N.C., USA).

The recombination rates provided in the manuscript are based upon the Oxford recombination rates calculated for HapMap release 16a. Estimates were generated separately from each of the four HapMap populations and then combined to give a single value. It states in the description of the recombination analysis track that differences in the recombination rate between populations were found to be not significant (see http://genome.ucsc.edu/cgi-bin/hgTrackUi?hgsid-103404772&c=chr10&g=snpRecombRate).

Population attributable risk (PAR) fractions were calculated for the combined replication panel (B-D) using the formula described by Rockhill and colleagues (Formula no. 3 in table 1 of 26). Using unconditional logistic regression, the best-fitting genetic model (dominant/recessive/additive) for the respective SNP was determined before. All six replicated SNPs (rs11805303, rs3024505, rs12612347, rs9268480, rs9268858, rs9268877) had the best model fit under a log-additive (or multiplicative) genetic model.

Mutation Detection

Amplicons were generated using the following touchdown PCR program:
95° C. for 12 min, (95° C. for 30 sec, Tm for 30 sec, 72° C. for 30 sec)×16 cycles [td −0.5° C.], (95° C. for 30 sec, Tm for 30 sec, 72° C. for 30 sec)×19 cycles, 72° C. for 10 min, 10° C. for ∞

Sequencing of genomic DNA was performed using Applied Biosystems BigDye™ chemistry according to the supplier's recommendations (for primer sequences, see table S5). Traces were inspected for the presence of SNPs and InDels using novoSNP[27].

Protein in-Silico Analysis

The multiple sequence alignment of the following IL10 protein homologs in the UniProtKB database (http://www.expasy.uniprot.org/) was created using the program MUSCLE (http://www.drive5.com/muscle/): human (P22301), chimpanzee (A2T6Z6), mouse (P18893), rat (P29456), cat (P55029), bovine (P43480), chicken (Q6A2H4), zebrafish (Q5EFQ8), equine herpesvirus 2 (EHV-2) (P68678), Epstein-Barr virus (EBV) (P03180), cercopithecine herpesvirus 12 (CeHV-12) (Q9Q5L1), ORF127 parapoxvirus (Orf virus) (Q6TVX3), lumpy skin disease virus (NW-LW) (Q77GR8), human cytomegalovirus (HCMV) (P17150).

The secondary structure assignment of human IL10 (PUB code 1j7v) was obtained from the DSSP database (http://www.cmbi.kun.nl/gv/dssp/) and added to the alignment. To predict the secondary structure of IL10 homologs, we applied the protein structure prediction server PSIPRED (http://bioinfcs.ucl.ac.uk/psipred/). The alignment was improved manually by minor adjustments based on multiple structure superimposition of the protein structures available for human IL10 (PDB 1j7v) and viral IL10 homologs (human cytomegalovirus, PDB 11qs; Epstein-Barr virus, PDB 1y6m) using MultiProt (http://bioinfo3d.cs.tau.ac.il/MultiProt/). Shading of sequence conservation was produced by GeneDoc (http://www.psc.edu/biomed/genedoc/).

The IL10 protein structure figure was prepared with PyMOL (http://www.pymoi.org). We used the crystal structure of human IL10 in complex with soluble IL10 RA (PDB code 1j7v). Biological unit coordinates were derived from the Protein Quaternary Structure file server (http://pqs.ebi.ac.uk/). The WHAT IF web server was employed for the calculation of interatomic contacts (http://swift.cmbi.ru.nl/).

LITERATURE TO SUPPLEMENTARY METHODS & MATERIALS

Incorporated Herein by Reference

1. Lennard-Jones, J. E. Classification of inflammatory bowel disease. *Scand J Gastroenterol Suppl* 170, 2-6; discussion 16-9 (1989).
2. Truelove, S. C. & Pena, A. S. Course and prognosis of Crohn's disease. *Gut* 17, 192-201 (1976).
3. 3. Krawczak, M. et al. PopGen: population-based recruitment of patients and controls for the analysis of complex genotype-phenotype relationships. *Community Genet* 9, 55-61 (2006).
4. Croucher, P. J. et al. Haplotype structure and association to Crohn's disease of CARD15 mutations in two ethnically divergent populations. *Eur J Hum Genet* 11, 6-16 (2003).
5. Hampe, J. et al. A genomewide analysis provides evidence for novel linkages in inflammatory bowel disease in a large European cohort. *Am J Hum Genet* 64, 808-16 (1999).
6. Hampe, J. et al. A genome-wide association scan of non-synonymous SNPs identifies a susceptibility variant for Crohn disease in ATG16L1. *Nat Genet* 39, 207-211 (2007).
7. Stoll, M. et al. Genetic variation in DLG5 is associated with inflammatory bowel disease. *Nat Genet* 36, 476-80 (2004).
8. Franke, A. et al. Systematic association mapping identifies NELL1 as a novel IBD disease gene. *PLoS ONE* 2, e691 (2007).
9. Mourn, B. et al. Incidence of ulcerative colitis and indeterminate colitis in four counties of southeastern Norway, 1990-93. A prospective population-based study. The Inflammatory Bowel South-Eastern Norway (IBSEN) Study Group of Gastroenterologists. *Scand J Gastroenterol* 31, 362-6 (1996).
10. Mourn, B. et al. Incidence of Crohn's disease in four counties in southeastern Norway, 1990-93. A prospective population-based study. The Inflammatory Bowel South-Eastern Norway (IBSEN) Study Group of Gastroenterologists. *Scand J Gastroenterol* 31, 355-61 (1996).
11. Onnie, C. M. et al. Associations of allelic variants of the multidrug resistance gene (ABCB1 or MDR 1) and inflammatory bowel disease and their effects on disease behavior: a case-control and meta-analysis study. *Inflamm Bowel Dis* 12, 263-71 (2006).
12. WTCCC. Genome-wide association study of 14,000 cases of seven common diseases and 3,000 shared controls. *Nature* 447, 661-78 (2007).
13. Vermeire, S. et al. Association of organic cation transporter risk haplotype with perianal penetrating Crohn's disease but not with susceptibility to IBD. *Gastroenterology* 129, 1845-53 (2005).
14. Stokkers, P. C. et al. Analysis of a positional candidate gene for inflammatory bowel disease: NRAMP2. *Inflamm Bowel Dis* 6, 92-8 (2000).
15. Weersma, R. K. et al. ATG16L1 and IL23R Are Associated With Inflammatory Bowel Diseases but Not With Celiac Disease in The Netherlands. *Am J Gastroenterol* 103, 621-7 (2008).
16. Dideberg, V. et al. An insertion-deletion polymorphism in the interferon regulatory Factor 5 (IRF5) gene confers risk of inflammatory bowel diseases. *Hum Mol Genet* 16, 3008-16 (2007).
17. Gazouli, M., Mantzaris, G., Archimandritis, A. J., Nasioulas, G. & Anagnou, N. P. Single nucleotide polymorphisms of OCTN1, OCTN2, and DLG5 genes in Greek patients with Crohn's disease. *World J Gastroenterol* 11, 7525-30 (2005).
18. Gazouli, M. et al. Association between polymorphisms in the Toll-like receptor 4, CD14, and CARD15/NOD2 and inflammatory bowel disease in the Greek population. *World J Gastroenterol* 11, 681-5 (2005).
19. Buch, S. et al. A genome-wide association scan identifies the hepatic cholesterol transporter ABCG5/ABCG8 as a susceptibility factor for human gallstone disease. *Nature Genetics in press* (2007).
20. de Bakker, P. I. et al. Efficiency and power in genetic association studies. *Nat Genet* 37, 1217-23 (2005).
21. Barrett, J. C., Fry, B., Mailer, J. & Daly, M. J. Haploview: analysis and visualization of LD and haplotype maps. *Bioinformatics* 21, 263-5 (2005).
22. Teuber, M. et al. Improving quality control and workflow management in highthroughput single-nucleotide polymorphism genotyping environments. *Journal of the Association for Laboratory Automation* 10, 43-47 (2005).
23. Dupont, W. D. & Plummer, W. D. PS power and sample size program available for free on the Internet. *Controlled Clin Trials* 18 (1997).
24. Purcell, S. et al. PLINK: a tool set for whole-genome association and population-based linkage analyses. *Am J Hum Genet* 81, 559-75 (2007).
25. Franke, A. et al. GENOMIZER: an integrated analysis system for genome-wide association data. *Hum Mutat* 27, 583-8 (2006).
26. Rockhill, B., Newman, B. & Weinberg, C. Use and misuse of population attributable fractions. *Am J Public Health* 88, 15-9 (1998).
27. Weckx, S. et al. novoSNP, a novel computational tool for sequence variation discovery. *Genome Res* 15, 436-42 (2005).

The invention claimed is:

1. A method of identifying individuals having a nucleic acid molecule, comprising:
  (a) amplifying a DNA fragment comprising an individual's nucleotide sequence selected from the group of:
    (i) nucleic acid molecules comprising the nucleotide sequence as depicted in SEQ ID NO: 2; and
    (ii) nucleic acid molecules the complementary strand of which hybridizes to a nucleic acid molecule of (i), using an oligonucleotide primer which specifically hybridizes to sequences within the individual's nucleotide sequence;
  (b) sequencing said amplified DNA fragment with dideoxy sequencing;
  (c) repeating steps (a) and (b) until the individual's nucleotide sequence is completely sequenced;
  (d) comparing the individual's nucleotide sequence with the nucleotide sequence as depicted in SEQ ID NO: 1;

(e) determining the presence of a polymorphic variation in the individual's nucleotide sequence at position 256 of the nucleotide sequence as depicted in SEQ ID NO: 4.

2. A method of identifying individuals having a nucleic acid molecule, comprising:
   (a) amplifying a DNA fragment comprising an individual's nucleotide sequence selected from the group of:
      (i) nucleic acid molecules comprising the nucleotide sequence as depicted in SEQ ID NO: 4; and
      (ii) nucleic acid molecules the complementary strand of which hybridizes to a nucleic acid molecule of (i),
   using an oligonucleotide primer which specifically hybridizes to sequences within the individual's nucleotide sequence;
   (b) sequencing said amplified DNA fragment with dideoxy sequencing;
   (c) repeating steps (a) and (b) until the individual's nucleotide sequence is completely sequenced;
   (d) comparing the individual's nucleotide sequence with the nucleotide sequence as depicted in SEQ ID NO: 3;
   (e) determining the presence of a polymorphic variation in the individual's nucleotide sequence at position 501 of the nucleotide sequence as depicted in SEQ ID NO: 4.

3. A method according to claim 1, wherein said oligonucleotide primer is labelled with a radiolabel, a fluorescent label, a bioluminescent label, a chemiluminescent label, or an enzyme label.

4. A method according to claim 2, wherein said oligonucleotide primer is labelled with a radiolabel, a fluorescent label, a bioluminescent label, a chemiluminescent label, or an enzyme label.

* * * * *